(12) United States Patent
Ichihashi et al.

(10) Patent No.: US 7,932,069 B2
(45) Date of Patent: Apr. 26, 2011

(54) PROCESS FOR PRODUCING LACTOPEROXIDASE

(75) Inventors: Nobuo Ichihashi, Isehara (JP); Koji Yamauchi, Kamakura (JP); Kouichirou Shin, Tokyo (JP); Tetsuya Ando, Zama (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 195 days.

(21) Appl. No.: 10/597,347

(22) PCT Filed: Feb. 8, 2005

(86) PCT No.: PCT/JP2005/002356
§ 371 (c)(1),
(2), (4) Date: Jul. 21, 2006

(87) PCT Pub. No.: WO2005/078078
PCT Pub. Date: Aug. 25, 2005

(65) Prior Publication Data
US 2008/0227171 A1    Sep. 18, 2008

(30) Foreign Application Priority Data

Feb. 17, 2004  (JP) .................. 2004-039704

(51) Int. Cl.
*C12N 9/04* (2006.01)
(52) U.S. Cl. ...................................... 435/190
(58) Field of Classification Search .................. None
See application file for complete search history.

(56) References Cited

U.S. PATENT DOCUMENTS

| | | | |
|---|---|---|---|
| 4,667,018 A | 5/1987 | Prieels et al. | |
| 4,791,193 A | 12/1988 | Okonogi et al. | |
| 5,149,647 A | 9/1992 | Burling | |
| 5,503,853 A | 4/1996 | Bollen et al. | |
| 5,516,675 A | 5/1996 | Uchida et al. | |
| 5,561,109 A | 10/1996 | Mita et al. | |
| 5,596,082 A | 1/1997 | Kussendrager et al. | |
| 5,780,593 A * | 7/1998 | Lihme et al. .............. | 530/361 |
| 6,010,698 A | 1/2000 | Kussendrager et al. | |
| 6,149,908 A | 11/2000 | Claesson et al. | |
| 7,247,331 B2 * | 7/2007 | Souppe .................. | 426/491 |

FOREIGN PATENT DOCUMENTS

| | | |
|---|---|---|
| EP | 0 253 395 A1 | 1/1988 |
| EP | 0390821 | 10/1990 |
| EP | 0518448 | 12/1992 |
| EP | 0556083 A1 | 8/1993 |
| JP | 2710283 | 3/1989 |
| JP | 2686831 | 5/1991 |
| JP | 3502921 | 7/1991 |
| JP | 3103615 | 4/1993 |
| JP | 3103167 | 5/1993 |
| JP | 5202098 | 8/1993 |
| JP | 2005202098 | 8/1993 |
| JP | 2985158 | 9/1993 |
| JP | 06-13560 | 6/1998 |
| JP | 2840795 | 12/1998 |
| JP | 3403066 | 1/1999 |
| JP | 2001226289 | 8/2001 |
| JP | 2002238554 | 8/2002 |
| JP | 2003246753 | 9/2003 |
| WO | 8904608 | 6/1989 |
| WO | 9201466 | 2/1992 |
| WO | 93/13676 A1 | 7/1993 |
| WO | 9726908 | 7/1997 |

OTHER PUBLICATIONS

Shin, Kouichirou, et al., "Purification and Quantification of Lactoperoxidase in Human Milk with use of Immunoadsorbents with Antibodies Against Recombinant Human Lactoperoxidase," The American Journal of Clinical Nutrition, 2001, vol. 73, pp. 984-989.
Supplementary European Search Report, PCT/JP2005002356, mailed Feb. 13, 2007 (3 pages); Letter from Stephanie Gadal to Shiga International Patent Office, Feb. 20, 2007, (1 page).
European Patent Office, Search Report and and Written Opinion in Application No. PCT/JP2005/002356, May 10, 2005, 9 pages.
Conner et al., Lactoperoxidase and Hydrogen Peroxide Metabolism in the Airway, "American Journal of Respiratory and Critical Care Medicine, USA", 2002, S57-61,vol. 166.
Wood et al., Evaluation of role of concentration and molecular weight of oat B-glucan in determining effect of viscosity on plasma glucose and insulin following an oral glucose load, "British Journal of Nutrition", 2000, pp. 19-23, vol. 84.
Lefkowitz et al., Peroxidase-Induced Enhancement of Chemiluminescence By Murine Peritoneal Macrophages, "Life Sciences", 1988, pp. 739-745, vol. 43.
Carlstrom, Lactoperoxidase: Identification of Multiple Molecular Forms and their Interrelationships, "Acta Chemica Scandinavica", 1969, pp. 171-184, vol. 23.
Paul et al., The Isolation and Some Liganding Properties of Lactoperoxidase, "FEBS Letters", 1980, pp. 200-204, vol. 110, No. 2.
Masae Kobayashi et al., "Simple Purification of Lactoperoxidase from Goat Milk," National Food Research Institute, 1999, pp. 99-101, vol. 46, No. 2.
Japanese Patent Office, Office Action for related Japanese Application No. 2005-518040, mailing date Aug. 8, 2006.
Hahn et al., Bovine whey fractionation based on cation-exchange chromatography, "Journal of Chromatography A", 1998, pp. 277-287, vol. 795.

* cited by examiner

*Primary Examiner* — Lisa J Hobbs
(74) *Attorney, Agent, or Firm* — Wood, Herron & Evans, LLP

(57) ABSTRACT

A process for producing lactoperoxidase, including: a step (1) for bringing one or more milk materials into contact with a cation exchanger having weakly acidic groups as ion exchange groups to thereby effect adsorption treatment; a step (2) for washing the cation exchanger after the adsorption treatment; a step (3) for bringing the cation exchanger after the washing into contact with a leaching solvent to thereby obtain a leaching solution having lactoperoxidase eluted into the leaching solvent; a step (4) for concentrating the leaching solution through an ultrafiltration membrane to thereby effect precipitation in the concentrated leaching solution; and a step (5) for obtaining a lactoperoxidase solution by removing the precipitation from the concentrated leaching solution.

16 Claims, No Drawings

PROCESS FOR PRODUCING LACTOPEROXIDASE

TECHNICAL FIELD

The present invention relates to a process for producing high purity lactoperoxidase from milk materials. Priority is claimed on Japanese Patent Application No. 2004-039704, filed Feb. 17, 2004, the content of which is incorporated herein by reference.

BACKGROUND ART

Lactoperoxidase is an oxidoreductase contained in mammalian milks such as cows milk, and other secretions such as saliva, lacrymal fluid, and respiratory tract mucus (for example, American Journal of Respiratory and Critical Care Medicine, U.S.A. Vol. 166, 2002, p.S57 to S61). Lactoperoxidase is a protein having a molecular weight of about 80,000. Lactoperoxidase has heme as a coenzyme per one molecule. Since the maximum absorption wavelength of this heme is about 412 nm, highly-purified lactoperoxidase exhibits a brown color (for example, British Journal of Nutrition, England, Vol. 84, 2000, p.S19 to S25).

It is reported that lactoperoxidase has various biological functions such as antibacterial properties, antiviral activity, antioxidative activity, anticancer activity, and immunoregulatory activity (for example, said British Journal of Nutrition, England, Vol. 84, 2000, p.S19 to S25, and Life Sciences, England, Vol. 43, 1988, p.739 to 745), and it is revealed that this is a very important protein in relation to host defense. Regarding the industrial application of such lactoperoxidase, there are disclosed techniques such as: use of lactoperoxidase, peroxide donor, and thiocyanate for the manufacture of a medicament for treating helicobacter pylori infection (for example, Published Japanese translation No. 2000-509367 of PCT); a preventive and therapeutic agent for infectious disease with pathogenic germs added to formula feed for cultured aquatic animals (for example, Japanese Patent No. 3103615); an aging preventing agent (for example, Japanese Patent No. 3103167); a hepatic function ameliorative agent (for example, Japanese Unexamined Patent Application, First Publication No. 2001-226289), prophylactic and therapeutic applications of peroxidases (for example, Published Japanese translation No. H06-501453 of PCT); and a therapeutic agent for corneal disorder (for example, Japanese Patent No. 2840795). Furthermore, there are disclosed techniques by the present inventors such as for: a urease-inactivating composition and a beverage (for example, Japanese Unexamined Patent Application, First Publication No. 2002-238554), and an intestinal flora improving agent and food and drink (for example, Japanese Unexamined Patent Application, First Publication No. 2003-246753).

Purification methods for lactoperoxidase in laboratory scale are reported in: Acta Chemica Scandinavica, Denmark, Vol. 23, 1969, p. 171 to 184; FEBS Letters, Holland, Vol. 110, 1980, p. 200 to 204; and Journal of Chromatography, Holland, Vol. 795, 1998, p. 277 to 287.

As a typical method thereof, there is known a method for: adding an acid such as hydrochloric acid into milk, to isoelectrically precipitate casein, so as to prepare whey serving as a supernatant; bringing the obtained whey into contact with a cation exchanger, so as to adsorb positively charged lactoperoxidase in the whey, into the cation exchanger; and next, washing the cation exchanger with a low salt buffer solution, and then desorbing the lactoperoxidase with a high salt buffer solution.

In a purification method in laboratory scale, in order to improve the lactoperoxidase purity, there is generally used a method for using a column which is highly densely filled with a cation exchanger in a gel form having small-diameter particles, and high-speed passing through is performed with a high pressure pump (for example, Journal of Chromatography, Holland, Vol. 795, 1998, p. 277 to 287).

On the other hand, if a column is filled with a cation exchanger having relatively large-diameter particles, and passing through is performed by means of natural drop without a high pressure pump, it takes more time (for example, Acta Chemica Scandinavica, Denmark, Vol. 23, 1969, p. 171 to 184, and FEBS Letters, Holland, Vol. 110, 1980, p. 200 to 204).

Together with the recent progress in isolation techniques at an industrial scale, it becomes possible to isolate and purify a high purity bioactive substance contained in milk, for mass production. In most cases, it is realistically difficult to scale up a protein purification method optimized at a laboratory scale into an industrial scale as it is. One of the main causes is that the property of an ion exchanger or a column generally used in a laboratory is not necessarily suitable for mass treatment of a raw material.

Furthermore, since addition of additives into milk materials tends to change the milk flavor and physical properties, it is not preferable to use additives for purifying a protein from milk materials. Furthermore, if a large amount of additives are used in order to wash a cation exchanger and/or to desorb a protein from the cation exchanger, it becomes necessary to remove these additives from the purified protein, and the production process becomes complicated.

As a production process for solving these problems in the production of a high purity protein from milk materials, there is already proposed by the present applicant, a production process for high purity bovine lactoferrin (for example, Japanese Examined Patent Application, Second Publication No. H06-13560).

Regarding the industrial production process for lactoperoxidase, the following are disclosed.

In the specification of U.S. Pat. No. 4,667,018, there is disclosed a process for purifying proteins such as lactoferrin and lactoperoxidase from milk or its milk derivative. In this process, there is disclosed a method for: bringing milk or its milk derivative into contact with a cation exchanger comprising cationic polysaccharides; washing the cation exchanger with a low salt solution; and then desorbing the proteins from the cation exchanger with a high salt solution. However, since the proteins produced in the method described in this Patent Document are obtained as a mixture, the purity is not high, and there is a problem in that high purity lactoperoxidase can not be produced.

In Japanese Patent No. 2985158, there is disclosed a method for recovering lactenin fraction having high activity. In this method described in this Patent Document, since lactoperoxidase is obtained as one component constituting lactenin, and contained in a protein mixture, there is also a problem in that high purity lactoperoxidase can not be produced.

In the specification of European Patent No. 0518448, as a method for isolating proteins from milk, there is disclosed a method of using a metal chelate carrier. In this method, since the isolated protein is a mixture comprising immunoglobulin, lactoferrin, and lactoperoxidase, there is a problem in that it is impossible to produce high purity lactoperoxidase.

In Japanese Patent No. 3403066, there is disclosed a method for recovering a cell-proliferating factor or a composition containing one or more kinds of cell-proliferating factors from milk or a milk derivative. However, since the composition obtained in this method is a mixture, there is also a problem in that this is not a process for producing high purity lactoperoxidase.

In Japanese Patent No. 2710283, as a method for selectively extracting a metal protein from whey, there is disclosed a method comprising a step for bringing whey into contact with inorganic porous particles (silica particles) coated with dextran comprising carboxyl groups or sulfonic groups. The purity of lactoperoxidase produced in this method is about 50% at the highest, and there is a problem in that, in order to produce high purity lactoperoxidase, it is necessary to increase the purity by another step.

In Japanese Patent No. 2553180, there is disclosed a process for extracting pure fractions of lactoperoxidase and lactoferrin from whey. In this process, as a means for solving the problem of clogging caused by volume change of a cation exchanger, a microfiltered whey is used as a milk material. In this process, since no milk material other than whey can be used, there is a problem of narrow application range. Furthermore, microfiltration is also required as a pretreatment of milk materials, complicating the production step. Moreover, a strong cation exchanger is used for the cation exchanger, and lactoperoxidase and lactoferrin are selectively desorbed by buffer solutions having different salt concentrations. This process requires, in order to wash the cation exchanger and to selectively desorb proteins, that the pH of the buffer solutions need to be adjusted, and therefore, a large amount of additives is used to prepare such buffer solutions. Moreover, there are various problems such that it is necessary to remove the additives from the purified proteins, serving as a factor of further complicating the step.

In Japanese Patent No. 2686831, there is disclosed a method for separating and purifying an iron binding protein using a strongly cationic sulfone group-introduced polysaccharides affinity carrier as a cation exchanger. In this method, a relatively highly purified (purity 85%) lactoperoxidase is produced. However, in a step for washing the cation exchanger after adsorption treatment, a washing treatment with a buffer solution adjusted to pH 5 or less is essential. Moreover, buffer solutions having respectively different salt concentrations of pH 5 or less are required for selectively desorbing lactoperoxidase and lactoferrin.

In Japanese Unexamined Patent Application, First Publication No. H05-202098, as a process for producing a bioactive substance from milk materials, there is disclosed a technique which can use either of a strong cation exchanger having sulfone groups and a weak cation exchanger having carboxyl groups. However, in this method, there is still a problem in that a buffer solution of pH 5 or less is required for enabling to wash the cation exchanger after adsorption treatment and to selectively desorb lactoperoxidase.

In U.S. Pat. No. 5,596,082, there is disclosed a process for isolating lactoferrin and lactoperoxidase from milk and milk products. In this patent, in order to enable to pass through milk and milk products at a high flow rate, a physically stable gel having large-diameter particles, is used as a cation exchanger. In this process, there is also a problem in that pH adjustment using a buffer solution is required for washing the cation exchanger after adsorption treatment and selectively desorbing lactoperoxidase. Since there is no description of the purity of lactoperoxidase produced in this patent, it is uncertain whether or not highly purified lactoperoxidase can be produced.

As described above, in most conventional processes for producing lactoperoxidase, lactoperoxidase recovered from milk materials is obtained as a mixture with other proteins, and the purity is not said to be sufficiently high. Moreover, in order to increase the purity of lactoperoxidase, other purification steps are required, thus requiring time and production costs therefor.

Moreover, even in the production process in which the purity of lactoperoxidase becomes relatively higher, there is also a problem in that pH adjustment is required in respective steps for; selectively adsorbing lactoperoxidase contained in milk materials, washing the cation exchanger, and selectively desorbing proteins, thus requiring use of a large amount of additives.

DISCLOSURE OF INVENTION

The present inventors have earnestly studied to solve the above problems. As a result, they have found a process which enables industrial production of high purity lactoperoxidase directly from milk materials, without performing pH adjustment, throughout the whole production steps, by performing treatment steps using an ion exchange method and an ultrafiltration membrane method, and have thus completed the present invention.

That is, a process for producing lactoperoxidase of the present invention comprises: a step (1) for bringing one or more milk materials into contact with a cation exchanger having weakly acidic groups as ion exchange groups to thereby effect adsorption treatment; a step (2) for washing the cation exchanger after the adsorption treatment; a step (3) for bringing the washed cation exchanger into contact with a leaching solvent which elutes lactoperoxidase, to thereby obtain a leaching solution having lactoperoxidase eluted into the leaching solvent; a step (4) for concentrating the leaching solution through an ultrafiltration membrane to thereby effect precipitation in the concentrated leaching solution; and a step (5) for obtaining a lactoperoxidase solution by removing the precipitation from the concentrated leaching solution.

BEST MODE FOR CARRYING OUT THE INVENTION

Hereunder is a detailed description of preferred examples of the present invention. However, the present invention is not limited to the following preferred examples, and may be freely modified within the scope of the present invention.

The present invention takes the problems and situations of conventional techniques into consideration, with an object of providing a process for producing lactoperoxidase, which enables production of highly purified lactoperoxidase with a simpler step, for a shorter time, at a lower cost than conventional processes, while preventing the change in the composition and the quality of milk materials wherein the change has been caused due to the usage of additives, and which can be applied to manufacture at an industrial scale.

Hereunder is a description of preferred conditions and obtained effects in the present invention.

In the present invention, preferably a lactoferrin adsorption capacity of the cation exchanger when 10 ml of the cation exchanger is put into 1 kg of unheated skim milk, is 85 mg/10 ml or more.

The ion exchange groups are preferably carboxymethyl groups.

In the step (4), preferably the concentration is performed so that a protein content in the leaching solution becomes 0.9 to 15%, to thereby effect precipitation.

Preferably the ionic strength of the leaching solvent used in the step (3) is 0.07 to 0.3.

Preferably the leaching solvent used in the step (3) is an aqueous solution containing at least one selected from a salt group consisting of sodium chloride, potassium chloride, calcium chloride, and magnesium chloride.

Preferably there is further provided a step for obtaining solid lactoperoxidase by removing the solvent of the lactoperoxidase solution obtained in the step (5).

Preferably the purity of the solid lactoperoxidase obtained in the above step is 80% or more.

In the present invention, when lactoperoxidase adsorbed into the cation exchanger is eluted into the leaching solvent, the lactoperoxidase is obtained in a mixture with other fractions (impurities). Then, when concentration is performed using an ultrafiltration membrane, the other fractions (impurities) are selectively isolated and removed by the difference in the solubility. As a result, high purity lactoperoxidase can be obtained.

Therefore, according to the present invention, the following effects can be obtained.

(1) Lactoperoxidase can be selectively recovered without going through a step requiring pH adjustment.

(2) High purity lactoperoxidase can be produced by a simple step, for a shorter time, at a lower cost.

(3) It is advantageous from the point of reducing the cost since no buffer solution nor a large amount of additives is required.

(4) Change in the composition and the quality of milk materials due to the usage of additives can be prevented.

(5) It can be readily applied at an industrial scale.

(6) It can be widely applied to milk materials other than whey, as a raw material to be in contact with the cation exchanger.

Next is a more detailed description of preferred examples of the present invention.

Regarding the protein content in the present specification, the nitrogen content in a sample was measured by the Kjeldahl method and indicated as a percentage that was converted using a nitrogen/protein conversion factor of 6.38.

Moreover, the purity of lactoperoxidase was analyzed by high performance liquid chromatography (HPLC), and indicated as a ratio (percentage) of a peak area of lactoperoxidase with respect to the total peak area derived from proteins in the sample.

In the present specification, the percentage other than the aforementioned protein content and purity is obtained based on mass, unless specifically explained.

As the milk materials that can be used in the present invention, anything containing at least lactoperoxidase can be used. For example, milk, skim milk, whey, and the like derived from mammals such as a human, a cow, a water buffalo, a sheep, a goat, and a horse may be used. Among them, one treated under a gentle heat treatment condition or an unheated one is preferably used. Moreover, there may be used a solution having skim milk powder, whole milk powder, whey powder, whey protein condensate (WPC), whey protein isolate (WPI), and the like dissolved in water or a buffer solution. Furthermore, there may be used a supernatant from which casein has been removed by isoelectric point precipitation, or by rennet, or a cheese whey drained at the time of cheese production. These milk materials can be used even without previously removing precipitations by a clarifier or by operations such as microfiltration and filtration.

In the present invention, in particular, bovine lactoperoxidase is preferably produced using milk material derived from a cow, as the milk material.

The milk material may be solely used, or plurality types thereof may be used in combination.

Hereunder is a description of the production process of the present invention.

(1) Firstly, milk material is brought into contact with a cation exchanger to thereby effect adsorption treatment. A cation exchanger having weakly acidic groups as ion exchange groups, is used. As the weakly acidic ion exchange group, it is possible to select any ion exchange group optionally insofar as the group can function as a suitable ion exchange group having an aimed purpose. Examples of the weakly acidic ion exchange group include a carboxyl group, a carboxymethyl group, a phenol group, and the like. It is preferably a carboxymethyl group.

The cation exchanger is not specifically limited, and may be optionally selected as required. Examples of preferred cation exchangers include porous particles comprising crosslinked polysaccharides (such as agarose, dextran, and cellulose), a hydrophilic silica gel, a synthetic polymer, and the like, that are introduced with weakly acidic ion exchange groups. As specific examples thereof, there may be preferably used SEPABEADS FP-CM13 (exchange groups: carboxymethyl group, made by Mitsubishi Chemical Corporation,), CM-Sephadex C-50 (exchange groups: carboxymethyl group, made by Amersham plc.), and CM-Sepharose-FF (exchange groups: carboxymethyl group, made by Amersham plc.).

The shape, size, surface condition, material, and the like of the cation exchanger are optional, and may be selected as required. Examples of the mode of usage include a pre-packed column in which a resin of an ion exchanger has been already filled, and a medium such as a column in which resin beads of cation exchanger are filled. In these cases, preferably one type of cation exchanger is used in combination with one vessel, from the viewpoint of convenience. However, as required, a plurality of vessels respectively filled with resin beads may be connected in series or in parallel, to perform chromatography. The shape of the vessel may be selected as required. However, preferably the shape is easy to wash, and gives many contact faces to resin beads or the like contained. Moreover, the inner wall preferably has a smooth surface without ruggedness. Specifically, shapes having a circular face such as a tubular shape (cylindrical and rod shape) and a conical shape may be preferably used as a shape of the vessels. The material of the vessel may be optionally selected, however there may be preferably used a stainless steel, a glass, polypropylene, polyethylene, polyethylene terephthalate, polycarbonate, an acrylic resin, and the like. The size of the vessel may be appropriately selected according to the scale of treatment, and may be optionally selected from scales such as several cubic centimeters to several cubic meters. Commercially available pre-packed columns that may be preferably used in the present invention, include HIPREP 10/16CM FF (exchange groups: carboxymethyl group, made by Amersham plc.), and CM-TOYOPEARLPAK650 series (exchange groups: carboxymethyl group, made by Tosoh Corporation).

Here, in order to increase the recovery rate of lactoperoxidase, preferably, in the following steps, when the cation exchanger after the adsorption treatment is brought into contact with a leaching solvent, proteins adsorbed into the cation exchanger are readily desorbed and eluted into the leaching solvent. Therefore, in the present invention, preferably proteins in milk materials are not too strongly bound to the cation exchanger. In a cation exchanger having strongly acidic groups as ion. exchange groups, the ion exchange groups are dissociated in a wide pH range. On the other hand, in a cation exchanger having weakly acidic groups as ion exchange groups, the electric charge varies depending on pH. As a result, it has a property of varying the protein binding capacity, and thus it is suitable in the production process of the present invention. In the present invention, it can be defined that an ion exchange group having an acid dissociation constant of less than 3 is a strongly acidic group, and an ion exchange group having an acid dissociation constant of 3 or more is a weakly acidic group. An example of the strongly acidic group includes a sulfonic group, and an example of the weakly acidic group includes a carboxymethyl group.

Moreover, the scale of porousness and adsorptivity of the cation exchanger used in the present invention may be optionally selected. Furthermore, the adsorption capacity with respect to a protein having approximately the same isoelectric point and molecular weight as those of lactoperoxidase, specifically, a protein having a molecular weight of 70 to 90 kDa, and an isoelectric point of 7 to 9, can be indicated as an index. Among them, the adsorption capacity with respect to lactoferrin (molecular weight: about 80 kDa, and isoelectric point: about 8) is preferably indicated as an index. The adsorption capacity of a cation exchanger with respect to lactoferrin may be obtained by for example, a method described in Japanese Examined Patent Application, Second Publication No. H06-13560.

That is, sodium type cation exchanger is swollen with water to make 10 ml, which is then put into 1 kg of unheated skim milk (pH 6.7). The mixed solution thereof is stirred at 4° C. for 16 hours. Then, the cation exchanger is preparatively isolated and washed with water. The washed cation exchanger is brought into contact with 150 ml of 10% concentration sodium chloride aqueous solution, so as to elute lactoferrin from the cation exchanger into the sodium chloride aqueous solution. The lactoferrin content in the collectate obtained by this elution, is measured by the Lowry method (Analytical Biochemistry, U.S.A. Vol. 15, 1966, p. 45 to 52), and thereby the adsorption capacity (unit: mg/10 ml) is calculated.

By selecting a cation exchanger having a higher lactoferrin adsorption capacity measured by the above method, the amount of recovered lactoperoxidase by the method of the present invention can be increased. That is, it is preferably a cation exchanger having a lactoferrin adsorption capacity of 70 mg or more when 10 ml of cation exchanger is put into 1 kg of unheated skim milk according to the above method, more preferably a cation exchanger having a lactoferrin adsorption capacity of 85 mg or more, and even more preferably a cation exchanger having a lactoferrin adsorption capacity of 90 mg or more. The value of the adsorption capacity is preferably higher. Generally, the lactoferrin content in 1 kg of milk is about 100 mg, and a cation exchanger capable of adsorbing its whole amount is ideal. Specifically, the lactoferrin adsorption capacity of the abovementioned SEPABEADS FP-CM13 is 85 mg/10 ml, and the lactoferrin adsorption capacity of the CM-Sephadex C-50 is 91 mg/10 ml. Both of them are cation exchangers showing a high lactoferrin adsorption capacity.

The adsorption treatment (contact) of the milk materials and the cation exchanger can be optionally selected. The adsorption treatment can be performed by a method such as a batch stirring method and a column continuous process. As long as the milk materials and the cation exchanger can be sufficiently in contact with each other, any treatment may be performed. One treatment may be performed, or a plurality of adsorption treatments may be performed in combination.

In the case of the batch type treatment, appropriately, a lot of cation exchanger is used in a case where a lot of yield is desired from a fixed amount of milk material, and a lot of milk material is used in a case where a lot of yield is desired with a fixed amount of cation exchanger. The mixing volume ratio of the milk materials and the cation exchanger in the batch type treatment can be optionally adjusted according to the adsorption capacity of the cation exchanger and/or a specific method of adsorption treatment.

Here, the property of the cation exchanger is largely classified into two types of hard type and soft type. In the present invention, either type can be used.

In the hard type, the volume of the ion exchanger itself is hardly changed due to the ionic strength or pH. Moreover, even if the pressure on the cation exchanger is changed due to the change in the flow rate or the like, the volume of the cation exchanger itself is hardly changed. Therefore, the hard type is more suitable for the column continuous process in which the cation exchanger is held in a column, and passing through is performed at a high flow rate.

On the other hand, in the soft type cation exchanger, the volume of the ion exchanger itself is largely changed due to the ionic strength or pH. Moreover, if the pressure on the cation exchanger is changed due to the change in the flow rate or the like, the volume of the cation exchanger itself is easily changed. Therefore, holding the soft type cation exchanger in a column and performing passing through at a high flow rate is difficult. In particular, in a case where skim milk, whey, or the like is passed through, a large pressure loss is caused in the cation exchanger layer compared to a case where other salt solution or the like is passed through. Therefore, the soft type cation exchanger is suitable for the batch method.

The SEPABEADS FP-CM13 (made by Mitsubishi Chemical Corporation) is a hard type, and the CM-Sephadex C-50 (made by Amersham plc.) is a soft type.

Regarding the temperature for the adsorption treatment of the milk materials and the cation exchanger, there is concern of an increase in the viscosity or freezing of the milk materials if it is less than 0° C., and there is a likelihood of denaturing lactoperoxidase if it exceeds 60° C. Therefore, the treatment is preferably performed within a range between 0° C. and 60° C. Even if it is between 25° C. and 60° C., in a case where a long time is required for adsorption, or the like, there may be a likelihood of gradually denaturing the lactoperoxidase. Therefore, the treatment is preferably performed, in particular at 0° C. to 25° C. Moreover, if unheated milk material is used, the treatment is desirably performed at 0° C. to 10° C. in order to prevent bacterial propagation.

Regarding the time for adsorption treatment (contact time) of the milk materials and the cation exchanger, conditions may be appropriately selected considering the temperature at the time of the adsorption treatment, the method of the adsorption treatment to be employed (batch type or column continuous process), and the like. For example, in a case of the batch type, the time for the adsorption treatment of the milk materials and the cation exchanger is preferably 1 minute or more but 24 hours or less, and more preferably 10 minutes or more but 6 hours or less. Moreover, in a case of the column continuous process, the linear flow rate is preferably 10 cm/h or more but 1000 cm/h or less.

(2) Next, the cation exchanger after the adsorption treatment is washed. As to the cleaning solution at this time, it is preferably washed with water considering the production cost, although it is possible to use a low salt aqueous solution having an ionic strength of less than 0.07, or a buffer solution in a neutral or weakly acidic region.

For the cation exchanger after the adsorption treatment, the used milk materials may be washed and removed by any method. For example, it may be such that only the cation exchanger is transferred from the container containing the milk materials and the cation exchanger, and then the cation exchanger is washed in another place, or it may be such that only the milk material is transferred from the container, and then the cation exchanger is washed in the container.

(3) Next, the washed cation exchanger is brought into contact with a leaching solvent. As a result, lactoperoxidase is eluted from the cation exchanger into the leaching solvent, and the leaching solution is obtained.

The ionic strength of the leaching solvent used in this step is preferably within a range of 0.07 or more but 0.3 or less, more preferably 0.10 or more but 0.25 or less, and even more preferably 0.15 or more but 0.22 or less. By using the leaching solvent having the ionic strength in the above range, lactoperoxidase can be efficiently eluted from the cation exchanger.

As to the leaching solvent, there may be also used a buffer solution in a neutral or weakly acidic region, having the ionic strength adjusted within the above range. Considering the production cost, more preferably, an aqueous solution (salt solution) having only salts dissolved can be used. Regarding the salts that can be used in the present application, one type or a combination of a plurality of types can be optionally selected.

The preferred salt solution is an aqueous solution of salt(s) comprising one type or a mixture of a plurality of types selected from a group consisting of sodium chloride, potassium chloride, calcium chloride, magnesium chloride, and the like.

(4) Next, a membrane treatment is performed on the obtained leaching solution by means of a membrane separation method through an ultrafiltration membrane. As a result, the leaching solution is concentrated, to thereby effect precipitation in the leaching solution.

The operation method of the ultrafiltration membrane can be classified into two of; a normal ultrafiltration method of letting water and components having a molecular weight of not more than the aimed molecular weight to be isolated, permeate to remove it, and a feeding water filtration method (diafiltration) of continuously operating while adding water of the same amount as that of the permeated matters that have permeated through the membrane, into the retentate on the membrane. Both method may be used in the present invention. In particular, the latter feeding water filtration method is more preferred from the point that desalting can be performed at the same time as concentration, and the low molecular weight components from the retentate can be removed to a high degree.

When the former normal ultrafiltration method is used, desalting is preferably performed by a method such as dialysis and gel filtration, after the ultrafiltration.

For the ultrafiltration membrane, any commercially available ultrafiltration membrane can be used. Specific examples thereof include IRIS3038 membrane, IRIS3072 membrane (both are made by Rhone-Poulenc S.A.), and GR-61pp membrane (made by DDS Inc.).

For the material of the ultrafiltration membrane, either organic material or inorganic material can be used, and may be selected considering the cost, generality, and the like.

The temperature of the leaching solution at the time of ultrafiltration treatment is feasible as long as it is not more than the heat resisting temperature of the membrane to be used (for example, 80° C. or less in the case of GR-61pp membrane). However, lactoperoxidase may be possibly denatured if it is 60° C. or more, and bacterial propagation tends to be significant within a range between 10 and 60° C. Therefore, it is preferably performed within a range between 0 and 10° C.

Regarding the pressure at the time of ultrafiltration, any pressure is possible as long as it is not more than the pressure proof limit of the membrane to be used (for example, 0.6 MPa or less in a case of GR-61pp membrane). Since usage around the pressure proof limit value may possibly shorten the membrane lifetime, ultrafiltration can be preferably performed at a pressure of ⅔ of the pressure proof limit (for example, 0.4 MPa or less in a case of GR-61pp membrane) or less.

For the module of the ultrafiltration membrane to be used, any type such as a tubular type, a hollow fiber type, a flat film type, and a spiral type is possible. However, in a module such as a hollow fiber type module which is internal pressure type, if precipitation is generated inside the hollow fiber, the passage might be possibly clogged, and therefore, ultrafiltration is preferably performed considering the pressure and the like.

The leaching solution obtained in the step (3) is preferably a clear brown solution. Moreover, when this leaching solution is concentrated through an ultrafiltration membrane, due to the difference in the protein solubility, proteins other than lactoperoxidase are precipitated as a precipitation in the retentate on the ultrafiltration membrane. Here, in order to efficiently precipitate proteins other than lactoperoxidase, that is, proteins as impurities, the concentration is preferably performed so that the protein content in the concentrated leaching solution becomes 0.9% or more. If the protein content in the leaching solution exceeds 15%, there is concern of an increase in the viscosity of the leaching solution, and thus a decrease in the efficiency of the ultrafiltration membrane treatment. Therefore, the protein content in the concentrated leaching solution is preferably within a range between 0.9 and 15%, more preferably 1.5 and 12%, and most preferably 3 and 10%.

By arranging the conditions in the respective steps until the precipitation is generated, the amount of lactoperoxidase mixed in the precipitation can be reduced, and it is also possible to generate precipitation containing no lactoperoxidase at all.

(5) Next, the precipitation is removed from the leaching solution (retentate) in which the precipitation has been generated. As a result, proteins as impurities are removed from the leaching solution, and a solution (lactoperoxidase solution) containing highly purified lactoperoxidase is obtained.

The method of removing the precipitation is optionally selected. It may be a method of removing the precipitation by leaving to stand the leaching solution (retentate) in which the precipitation has been generated, or it may be a method of collecting a clarified solution (lactoperoxidase solution) from which the precipitation has been removed, by performing a clarification treatment by means of centrifugation, precise filtration (microfiltration), or the like.

The lactoperoxidase solution obtained by this step is preferably sterilized as required. At this time, from the viewpoint of increasing the thermal stability of lactoperoxidase, the sterilization is preferably performed such that calcium ions such as calcium chloride are added to make the concentration of about 20 mM, and heat sterilization is performed at 72° C. for about 15 to 90 seconds.

(6) Then, solid lactoperoxidase can be obtained by removing the solvent of the obtained lactoperoxidase solution.

The method of removing the solvent is not specifically limited and may be selected as required. For example, there may be suitably used a method of further concentrating using an ultrafiltration membrane, and freeze-drying by a normal method, so as to remove moisture. As a result, highly purified lactoperoxidase powder can be produced.

The solid lactoperoxidase obtained in this manner can achieve a high purity of 80% or more.

The step (6) for removing the solvent is not essential. The lactoperoxidase solution obtained as highly purified lactoperoxidase in step (5) may be used as it is in solution state.

EXAMPLES

Next is a detailed description of the present invention by showing test examples. However, the present invention is not limited to the following examples. For example, in the present application, the components in these examples and components not included in the examples may be appropriately combined. Moreover, except for the protein content and the purity, % denotes mass % unless specifically described.

Test Example 1

The present test was performed to examine the preferable conditions for producing precipitation in the step (4), which was conducted following the steps (1) to (3), for generating a precipitation in the concentrate by concentrating the leaching solution collected from the weakly acidic cation exchanger, through an ultrafiltration membrane.
(1) Sample As a weakly acidic cation exchanger, CM-Sephadex C-50 (made by Amersham plc.) having carboxymethyl groups and the lactoferrin adsorption capacity of 91 mg/10 ml, was used.

A column filled with 170 ml of the weakly acidic cation exchanger was added with 20 liters of skim milk, so as to adsorb proteins into the exchanger. Next, the weakly acidic cation exchanger in the column was washed with water, then 200 ml of 1.6% sodium chloride aqueous solution (ionic strength 0.27) as a leaching solvent was added into the column, so that the proteins that had been adsorbed into the weakly acidic cation exchanger were eluted into the sodium chloride aqueous solution. About 200 ml of the collected leaching solution was used as the test sample. The protein content in the obtained test sample was measured by the Kjeldahl method, and it was 0.26%.
(2) Test Method Three types of centrifugal type ultrafiltration filter units (fractional molecular weight: 10K Dalton, 30K Dalton, and 50K Dalton, all of which were made by Millipore Corporation) were prepared.

0.5 ml of test sample was added to each filter unit, and ultrafiltration was performed by centrifugation at 6000 rpm. Then, the presence/absence of precipitation generation was observed. At this time, by controlling the centrifugation time, the volume of the retentate in the filter unit was changed in stages.
(3) Test Result As a result of the present test, in any one of the three filter units having different fractional molecular weights, when the volume of the retentate in the filter unit was concentrated to 0.15 ml, a white precipitation was observed on the filter. When the volume of the retentate was 0.15 ml or less, precipitation generation was also observed. However, when it was more than 0.15 ml, no precipitation was observed.

Moreover, when the volume of the retentate was concentrated to 0.15 ml, the total protein content in the retentate was 0.9%.

From this result, it was confirmed that, when the concentration was performed so that the total protein content in the concentrated retentate became 0.9%, precipitation was generated in the retentate.

Test Example 2

The present test was performed to examine the effect of desalting treatment on the solubility of the precipitation generated by the concentration using the ultrafiltration membrane.
(1) Sample For the sample of the present test, a similar test sample to that of the Test Example 1 (leaching solution having proteins eluted in 1.6% sodium chloride aqueous solution, protein content: 0.26%) was used.

(2) Test Method

Three stirred cell units (made by Millipore Corporation) attached with an ultrafiltration membrane of 30K Dalton fractional molecular weight, were prepared. Each cell unit was added with 50 ml of test sample. Using nitrogen gas, the inside of the cell unit was pressurized to about 0.3 MPa, and the retentate in the cell unit was concentrated to 10 ml.

Regarding the first cell, when the retentate became 10 ml, the whole amount of the retentate in the cell unit was transferred into a centrifugal tube, and separated into solid and liquid by centrifugation at 10,000 rpm. Then, the precipitation (precipitation sample 1) was collected.

Regarding the second cell, when the retentate became 10 ml, the whole amount of the retentate in the cell unit was transferred into a centrifugal tube, and separated into solid and liquid by centrifugation at 10,000 rpm. Then, the precipitation was collected. The precipitation was added with 10 ml of purified water, and stirred by a vortex mixer for 1 minute. The precipitation suspension obtained in this manner was moved into a centrifugal tube, and further separated into solid and liquid by centrifugation at 10,000 rpm. Then, the precipitation (precipitation sample 2) was collected.

Regarding the third cell, 40 ml of purified water was added in the cell unit having the retentate concentrated to 10 ml. It was then pressurized similarly to the previous time, until the retentate was concentrated to 10 ml again. When the retentate became 10 ml, the whole amount of the retentate in the cell unit was transferred into a centrifugal tube, and separated into solid and liquid by centrifugation at 10,000 rpm. Then, the precipitation (precipitation sample 3) was collected.

The dry weight of the precipitation samples 1 to 3 was measured by a normal method.
(3) Test Result As a result of the present test, in any cell, when the retentate in the cell unit was 10 ml, precipitation was formed in the retentate.

Moreover, there was almost no difference in the mass of the precipitation samples 1 to 3. Consequently, it was confirmed that, even if purified water was added into the precipitation that had been once formed by the concentration step, the precipitation was not re-dissolved.

Furthermore, it was confirmed that the precipitation that had been once formed in the leaching solution, was not affected even if the salt level was changed by desalting, and the precipitation was not re-dissolved.

Next is a more detailed description of the present invention by showing examples. However, the present invention is not limited to the following examples.

Example 1

As a weakly acidic cation exchanger, CM-Sephadex C-50 (made by Amersham plc.) having carboxymethyl groups and the lactoferrin adsorption capacity of 91 mg/10 ml, was used.

17 liters of this cation exchanger was filled into a column having an inner diameter of 50 cm, and 40 liters of 1.5% sodium chloride aqueous solution was passed through the column. Then, it was washed with water, and the cation exchanger in the column was adjusted into the sodium form.

Skim milk (pH 6.7, sample 1 described later) derived from a cow was prepared as the milk material. 2000 liters of this skim milk was passed through the column under the condition of the temperature at 4° C. and the flow rate at 60 liter/h, to thereby effect adsorption treatment.

Water was passed through the column after the adsorption treatment, so as to wash the milk components that had not been specifically adsorbed into the cation exchanger.

Next, 20 liters of 1.6% sodium chloride aqueous solution (ionic strength 0.27) as the leaching solvent was passed through at a flow rate of 30 liter/h, so as to elute the proteins adsorbed into the cation exchanger. As a result, 21 liters of the leaching solution (sample 2 described later) containing bovine lactoperoxidase was collected.

Next, 21 liters of the leaching solution was ultrafiltrated using an ultrafiltration membrane (made by DDS Inc.) unit of 20K Dalton fractional molecular weight, at an average pressure of 0.3 MPa, and concentration was performed until the amount of the retentate became 2 liters.

Then, ultrafiltration was further performed while adding water, so as to desalt the retentate, and finally 2 liters of the retentate was collected. A white precipitation was generated in the retentate.

Next, the retentate containing the while precipitation was left standing to clarify, and 1.95 liters of the supernatant fraction (sample 3 described later) was collected as bovine lactoperoxidase solution.

The collected supernatant fraction (bovine lactoperoxidase solution) was microfiltrated using a precise filtration membrane having a pore size of 1.4 μm, to further remove smaller amounts of precipitation, and the purified preparation containing bovine lactoperoxidase was produced.

Furthermore, the obtained purified preparation was freeze-dried, to produce 26 g of powdery freeze-dried preparation (sample 4 described later) containing bovine lactoperoxidase.

Regarding the above samples 1 to 4 obtained during the production steps, that is, sample 1: skim milk (milk material), sample 2: leaching solution from the cation exchanger, sample 3: supernatant fraction of retentate after ultrafiltration membrane treatment, and sample 4: freeze-dried preparation, the protein content and the bovine lactoperoxidase activity were measured for each to obtain the specific activity. Here, the protein content was measured by the Kjeldahl method, and the bovine lactoperoxidase activity was measured by a method of Putter et. al. (Bergmeyer ed, Methods of Enzymatic Analysis, third edition, Vol. 3, 1983, p. 286 to 293), to obtain the peroxidase activity (specific activity) per 1 mg protein. The results are shown in Table 1.

TABLE 1

| Sample | Protein content (%) | Specific activity (unit/mg) |
| --- | --- | --- |
| Sample 1 | 3.30 | 0.2 |
| Sample 2 | 0.26 | 132.5 |
| Sample 3 | 1.64 | 220.3 |
| Sample 4 | 92.30 | 224.4 |

As shown in Table 1, the protein content of sample 1 was 3.30% and the specific activity thereof was 0.20 unit/mg. Moreover, the protein content of sample 2 was 0.26% and the specific activity thereof was 132.5 unit/mg. From these results, it is understood that, among the proteins in the skim milk (milk material), bovine lactoperoxidase was selectively eluted in the leaching solution.

Moreover, the protein content of sample 3 was 1.64% and the specific activity thereof was 220.3 unit/mg. The specific activity of sample 4 was 224.4 unit/mg.

Comparing the results of sample 2, and samples 3 and 4, by concentrating the leaching solution using the ultrafiltration membrane, and removing the generated precipitation, the specific activity of bovine lactoperoxidase is remarkably increased. As a result, it is understood that, by such removal of precipitation, proteins as impurities other than bovine lactoperoxidase are effectively removed, and the purification efficiency of bovine lactoperoxidase is increased.

Moreover, regarding the sample 4 (freeze-dried preparation), the purity of lactoperoxidase was analyzed by high performance liquid chromatography.

In this analysis, there was used a HPLC apparatus equipped with a SHODEX ASAHIPAK C4P-50 column and an ultraviolet absorption detector having an assay wavelength of 280 nm. Regarding the mobile phase, the flow rate was 0.8 ml/min, and the elution was performed by a linear density gradient method having the concentration change wherein the ratio A:B was changed from 50:50 to 0:100 in 30 minutes, using A solution (mixed solution of acetonitrile:0.5M sodium chloride=10:90, containing 0.03% trifluoroacetic acid) and B solution (mixed solution of acetonitrile:0.5M sodium chloride=50:50, containing 0.03% trifluoroacetic acid). About 20 mg of the sample was weighted and dissolved in 10 ml of 2.9% sodium chloride aqueous solution, 25 μl of which was tested in the above analysis method.

Here, purified bovine lactoperoxidase (made by Sigma-Aldrich Co.) was previously used as a reference standard, to confirm that the peak of the reference standard was about 18 minutes of elution time in the above analysis method.

Next, the sample 4 was analyzed in the above analysis method and the bovine lactoperoxidase purity was measured by automatic integration regarding the peak area.

As a result, it was confirmed that the bovine lactoperoxidase purity of sample 4 was 89%. Consequently, it was confirmed that highly purified lactoperoxidase could be produced from milk materials by the method of the present invention.

INDUSTRIAL APPLICABILITY

The present invention provides a process for producing lactoperoxidase, which enables to produce highly purified lactoperoxidase with a simpler step, for a shorter time, at a lower cost than conventional processes, and which can be applied to manufacture at an industrial scale.

The invention claimed is:

1. A process for producing lactoperoxidase comprising:
   a step (1) for bringing one or more milk materials, which include lactoperoxidase, into contact with a cation exchanger having weakly acidic groups as ion exchange groups to thereby effect adsorption of the lactoperoxidase;
   a step (2) for washing the cation exchanger after said adsorption of the lactoperoxidase;
   a step (3) for bringing said washed cation exchanger into contact with a leaching solvent which elutes the lactoperoxidase, wherein an ionic strength of the leaching solvent is 0.07 to 0.3, to thereby obtain a leaching solution, which includes the lactoperoxidase;
   a step (4) for concentrating said leaching solution by passing a portion of said leaching solution through an ultrafiltration membrane so that the protein content in said concentrated leaching solution, which is retentate, becomes 0.9 to 15%, and wherein proteins other than the lactoperoxidase precipitate out in the retentate; and
   a step (5) for obtaining a lactoperoxidase solution by removing the precipitate from the retentate.

2. A process for producing lactoperoxidase according to claim 1, wherein a lactoferrin adsorption capacity of said cation exchanger is 85 mg/10 ml or more.

3. A process for producing lactoperoxidase according to claim 1, wherein said ion exchange groups are carboxymethyl groups.

4. A process for producing lactoperoxidase according to claim 2, wherein said ion exchange groups are carboxymethyl groups.

5. A process for producing lactoperoxidase according to claim 1, wherein the leaching solvent used in said step (3) is an aqueous solution containing at least one salt selected from a group consisting of sodium chloride, potassium chloride, calcium chloride, and magnesium chloride.

6. A process for producing lactoperoxidase according to claim 2, wherein the leaching solvent used in said step (3) is an aqueous solution containing at least one salt selected from a group consisting of sodium chloride, potassium chloride, calcium chloride, and magnesium chloride.

7. A process for producing lactoperoxidase according to claim 3, wherein the leaching solvent used in said step (3) is an aqueous solution containing at least one salt selected from a group consisting of sodium chloride, potassium chloride, calcium chloride, and magnesium chloride.

8. A process for producing lactoperoxidase according to claim 1, further comprising a step for obtaining solid lactoperoxidase by removing the solvent of the lactoperoxidase solution obtained in said step (5).

9. A process for producing lactoperoxidase according to claim 2, further comprising a step for obtaining solid lactoperoxidase by removing the solvent of the lactoperoxidase solution obtained in said step (5).

10. A process for producing lactoperoxidase according to claim 3, further comprising a step for obtaining solid lactoperoxidase by removing the solvent of the lactoperoxidase solution obtained in said step (5).

11. A process for producing lactoperoxidase according to claim 5, further comprising a step for obtaining solid lactoperoxidase by removing the solvent of the lactoperoxidase solution obtained in said step (5).

12. A process for producing lactoperoxidase according to claim 8, wherein a purity of the solid lactoperoxidase is 80% or more.

13. A process for producing lactoperoxidase according to claim 9, wherein a purity of the solid lactoperoxidase is 80% or more.

14. A process for producing lactoperoxidase according to claim 10, wherein a purity of the solid lactoperoxidase is 80% or more.

15. A process for producing lactoperoxidase according to claim 11, wherein a purity of the solid lactoperoxidase is 80% or more.

16. A process for producing lactoperoxidase according to claim 1, wherein no buffer solution is used in any step of (1) to (5).

* * * * *